(12) United States Patent
Van Gogh et al.

(10) Patent No.: US 8,318,143 B2
(45) Date of Patent: Nov. 27, 2012

(54) COMPOSITIONS FOR TREATING KERATIN-CONTAINING FIBERS AND MAINTAINING DYED FIBER COLOR INTEGRITY

(75) Inventors: Kelly Van Gogh, New York, NY (US); William Onyebuagu, Chicago, IL (US)

(73) Assignee: Kelly Van Gogh Hair Colour Cosmetics, Inc., Santa Monica, CA (US)

( * ) Notice: Subject to any disclaimer, the term of this patent is extended or adjusted under 35 U.S.C. 154(b) by 89 days.

(21) Appl. No.: 12/875,069

(22) Filed: Sep. 2, 2010

(65) Prior Publication Data

US 2012/0058067 A1    Mar. 8, 2012

(51) Int. Cl.
*A61Q 5/02* (2006.01)
*A61Q 5/12* (2006.01)

(52) U.S. Cl. ............. 424/70.19; 424/70.21; 424/70.24; 424/70.31; 424/70.12

(58) Field of Classification Search .................. None
See application file for complete search history.

(56) References Cited

U.S. PATENT DOCUMENTS

| | | |
|---|---|---|
| 4,009,256 A * | 2/1977 | Nowak et al. ............ 510/122 |
| 4,776,856 A | 10/1988 | Tennigkeit et al. |
| 4,808,190 A | 2/1989 | Grollier et al. |
| 5,529,583 A | 6/1996 | Lim et al. |
| 5,618,523 A | 4/1997 | Zysman et al. |
| 5,672,180 A | 9/1997 | Lim et al. |
| 6,045,590 A | 4/2000 | Lim et al. |
| 6,251,378 B1 | 6/2001 | Laurent et al. |
| 6,312,677 B1 | 11/2001 | Millequant et al. |
| 6,537,328 B1 | 3/2003 | Lang et al. |
| 6,554,871 B2 | 4/2003 | Braun |
| 7,060,108 B2 | 6/2006 | Morita et al. |
| 7,179,302 B2 | 2/2007 | Boswell et al. |
| 7,186,275 B2 | 3/2007 | Boswell et al. |
| 7,429,276 B2 | 9/2008 | Wood et al. |
| 2007/0020208 A1 | 1/2007 | Gutkowski et al. |
| 2008/0034510 A1 | 2/2008 | Speckbacher et al. |
| 2008/0194708 A1 | 8/2008 | Hossel et al. |
| 2008/0247982 A1 * | 10/2008 | Lang ..................... 424/70.28 |
| 2009/0068136 A1 | 3/2009 | Beumer et al. |
| 2010/0040573 A1 | 2/2010 | Garcia Castro et al. |

* cited by examiner

*Primary Examiner* — Jyothsna Venkat
(74) *Attorney, Agent, or Firm* — Richard S. Echler

(57) ABSTRACT

Disclosed are compositions, inter alia, shampoos, conditioners, and restoratives that are effective in preventing further damage to keratin-containing fibers damaged by exposure to oxidative dyeing catalysts, mechanical damage, exposure to UV and visible radiation, and the like.

1 Claim, No Drawings

COMPOSITIONS FOR TREATING KERATIN-CONTAINING FIBERS AND MAINTAINING DYED FIBER COLOR INTEGRITY

FIELD

Disclosed are compositions, inter alia, shampoos, conditioners, and restoratives that are effective in preventing further damage to keratin-containing fibers damaged by exposure to oxidative dyeing catalysts, mechanical damage, exposure to UV and visible radiation, and the like.

BACKGROUND

Melanin is a class of naturally occurring polymers that are responsible for the coloring of natural tissue, inter alia, skin and hair. Depending upon the chemical make-up of the particular polymer, the resulting pigment can have a wide range of colors, i.e., very light to very dark (for example, black). In keratin-containing fibers such as human hair, melanin is produced together with the hair-forming cells in the hair bulb located at the root of the hair fiber. When new hair cells are formed, older cells move upward and form the fiber shaft which extends above the skin surface, for example, the scalp. Hair comprises a central cortex containing the melanin and an outer cuticle. The particular composition of the cortex provides keratin-containing fibers with their particular physical properties, inter alia, whether the fibers are straight or are curled.

The dead cells which comprise the keratin-containing fibers of hair are proteins that comprise high concentrations of cystine which is the natural crosslinking of two cysteine amino acids located on different protein chains via a disulfide bond. The strength and rigidity of hair is a result of a high concentration of these crosslinks.

Humans, as they grow older, produce less and less melanin resulting in hair developing a gray to white color. Dark keratin-containing fibers can be deliberately lightened by chemical treatment, for example, by contacting the fibers with an oxidizing agent that breaks down the polymeric backbone of melanin. "Bleaching" of human hair to lighten the color or hue of the fibers can be accomplished by contacting the fibers with any one of several oxidizing agents, inter alia, hydrogen peroxide, potassium, sodium or ammonium salts of perborate or percarbonate, persulfate and percarbamide.

During the process of dyeing, tinting, or otherwise coloring keratin-containing fibers, oxidizing agents are used to produce the final colorant from an admixture of colorant precursors. These precursors are typically low molecular weight molecules that diffuse into the interstices of the fibers where they react with one another due to the presence of an oxidative catalyst, for example, hydrogen peroxide. Colorant formulations are typically comprised of one or more agents capable of swelling the keratin-containing fibers to facilitate the diffusion of the precursor molecules into the fiber pores.

This process for changing the color, tint, or hue of keratin-containing fibers has been successfully used for many years; however, the presence of the oxidative catalyst also provides a means for damaging the keratin polymers themselves. Repeated exposure to the oxidative catalysts contained in dyeing compositions can lead to a cumulative breakdown of the keratin-containing fibers. As a remedy, post oxidative dyeing compositions such as shampoos and conditioners have been developed in an attempt to restore the original hair fiber properties. One drawback to these compositions is that they can simply coat the outside of the keratin-containing fibers thereby providing a "masking" of the actual fiber damage. The use of cleansing, conditioning, and maintenance compositions that are ineffective in repairing fiber damage can provide a desirable texture without actually repairing or fortifying the damaged fibers.

Therefore, there is a long felt need for compositions that can be applied to keratin-containing fibers damaged by exposure to oxidative catalysts to restore the fibers to their original pre-treatment conditions. In addition, there is a long felt need for compositions which can provide protection against further damage to fibers while providing effective cleaning and conditioning of the fibers.

DETAILED DESCRIPTION

The materials, compounds, compositions, articles, kits and methods described herein may be understood more readily by reference to the following detailed description of specific aspects of the disclosed subject matter and the Examples included therein.

Before the present materials, compounds, compositions, articles, devices, kits and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

All values in the disclosed TABLES are in weight/weight percentage, i.e., "a composition comprising 15% by weight" is understood to comprise 0.15 of its mass the disclosed ingredient. As such, a weight percent of a component, unless specifically stated to the contrary, is based on the total weight of the formulation or composition in which the component is included.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Admixture" or "blend" is generally used herein means a physical combination of two or more different components.

As used herein, by a "subject" is meant an individual, i.e., a human or animal having keratin-containing fiber (in general, hair) onto which subject's fibers is being applied one or more of the disclosed compositions.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "a phenylsulfamic acid" includes mixtures of two or more such phenylsulfamic acids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "keratinous tissue," as used herein, refers to keratin-containing layers disposed as the outermost protective covering of mammals which includes, but is not limited to, skin, hair, toenails, fingernails, cuticles, hooves, etc.

The term "colorant precursor," as used herein, means compounds that can function as oxidative dye precursors, coupling agents, or in some instances the compounds can function as both oxidative dye precursors and coupling agents. The disclosed colorant precursors react with one another in a manner understood by the formulator when acted upon by a catalyst to form compound admixtures that provide a dye, hue, tint, color, and the like to keratin-containing fibers.

The term "topical application," as used herein, means to apply or spread the compositions of the present invention onto the surface of the keratinous tissue.

The term "dermatologically acceptable," as used herein, means that the compositions or components thereof so described are suitable for use in contact with human keratinous tissue.

The term "safe and effective amount" as used herein means an amount of a compound or composition sufficient to significantly induce a positive benefit.

The term "active ingredient," as used herein, relates to compounds that either alone or together with one or more of the disclosed ingredients is capable of modifying keratin-containing fibers or can modify or improve the application of the composition including stabilizing one or more of the other ingredients, for example, an active ingredient can be a compound that stabilizes the hydrogen peroxide or that maintains a homogeneous composition by eliminating phase separation or undesirable micelle formation. Not included in the definition of "active ingredients" are compounds that are used to dilute or aid in the dissolution of ingredients, for example, water is not an active ingredient.

The term "smoothing" and "softening" as used herein means altering the surface of the keratinous tissue such that its tactile feel is improved.

Disclosed herein are compositions useful for restoring damaged keratin-containing fibers that have been oxidatively dyed, especially human hair wherein the compositions provide a means for maintaining a durable and homogeneous color.

There is a long felt need for maintaining the color of keratin-containing fibers after oxidative dyeing. "Permanent" colorant compositions are not truly permanent. Hair colorant products typically use oxidative dye color precursors that are small enough to penetrate the surface of the keratin-containing fibers and provide the instantaneous change the consumer desires. Due to the small size of the precursor molecules, however, they are easily leached out of the fibers, leading to fading or a change in tone upon exposure to physical, mechanical or chemical damage. Therefore, it is desirable to minimize this change and loss of color. Furthermore, there is unavoidable damage to the cuticles associated with the process of hair coloring, which often leaves hair harder to manage and more difficult to comb. Hence there is a long felt need for products that overcome the deleterious effects of the coloring process on keratin-containing fibers while serving to preserve the color, tint, or hue.

The first category of compositions of the present disclosure relates to keratin-containing fiber cleansing compositions. The cleansing compositions can be shampoos, scrubs, comb-in cleaners, anti-grime treatments, and the like.

A first aspect of the cleaning compositions relates to compositions comprising:
- A) from about 25% to about 60% by weight of a surfactant system;
- B) from about 0.5% to about 15% by weight of one or more composition modifiers;
- C) from about 0.5% to about 10% by weight of one or more keratin-containing fiber enhancement ingredients; and
- D) the balance one or more carriers.

In one embodiment of this aspect, the compositions comprise:
- A) from about 25% to about 90% by weight of a surfactant system, comprising:
  - a) from about 25% to about 60% by weight of one or more anionic surfactants;
  - b) from about 15% to about 45% by weight of one or more zwitterionic (amphoteric) surfactants;
  - c) from about 0.5% to about 10% by weight of one or more nonionic surfactants; and
  - d) from about 5% to about 15% by weight of one or more cationic surfactants;
- B) from about 0.5% to about 15% by weight of a composition modifier system comprising:

a) from about 10% to about 50% by weight of one or more thickeners;
b) from about 25% to about 90% by weight of a foaming agent; and
c) optionally from about 5% to about 15% by weight of one or more aesthetic agents;

C) from about 0.5% to about 10% by weight of a keratin-containing fiber enhancement system comprising:
a) from about 10% to about 50% by weight of one or more emollients and/or humecticants;
b) from about 10% to about 50% by weight of one or more wetting agents;
c) from about 10% to about 50% by weight of one or more antistatic agents; and D) the balance one or more carriers.

One iteration of this embodiment relates to compositions comprising:

A) from about 25% to about 60% by weight of a surfactant system, comprising:
a) from about 40% to about 90% by weight of one or more anionic surfactants chosen from:
i) $C_{10}$-$C_{18}$ alkyl alkoxy sulfates having the formula:

$$CH_3(CH_2)_x(OCH_2CH_2)_yOSO_3M$$

wherein the index x is from 9 to 17, y is from 1 to 7 and M is a water soluble cation chosen from ammonium, lithium, sodium, potassium and mixtures thereof; and ii) $C_{10}$-$C_{18}$ alkenyl sulfonates (α-olefin sulfonates) having the formula:

$$CH_3(CH_2)_zCH=CHSO_3M$$

wherein the index z is from 7 to 15 and M is a water soluble cation chosen from ammonium, lithium, sodium, potassium and mixtures thereof;

b) from about 15% to about 45% by weight of one or more $C_{10}$-$C_{16}$ alkyl amide betaine zwitterionic surfactants having the formula:

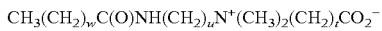

$$CH_3(CH_2)_wC(O)NH(CH_2)_uN^+(CH_3)_2(CH_2)_tCO_2^-$$

wherein the index w is from 9 to 15, the index u is from 1 to 5 and the index t is from 1 to 5; and c) from about 0.5% to about 10% by weight of a $C_8$-$C_{18}$ alkylglycosidyl nonionic surfactant having the formula:

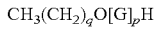

$$CH_3(CH_2)_qO[G]_pH$$

wherein G represents a monosaccharide residue chosen from glucose, fructose, mannose, galactose, talose, allose, altrose, idose, arabinose, xylose, lyxose, ribose and mixtures thereof, the index p is from 1 to 4, and the index q is from 7 to 17;

B) from about 0.5% to about 15% by weight of a composition modifier system comprising:
a) from about 10% to about 50% by weight of one or more thickeners;
b) from about 25% to about 90% by weight of a foaming agent; and
c) optionally from about 5% to about 15% by weight of one or more aesthetic agents;

C) from about 0.5% to about 10% by weight of a keratin-containing fiber enhancement system comprising:
a) from about 10% to about 50% by weight of one or more emollients and/or humecticants;
b) from about 10% to about 50% by weight of one or more wetting agents;
c) from about 10% to about 50% by weight of one or more antistatic agents; and D) the balance one or more carriers.

Another iteration of this embodiment relates to compositions comprising:

A) from about 25% to about 60% by weight of a surfactant system, comprising:
a) from about 55% to about 75% by weight of one or more anionic surfactants chosen from:
i) sodium $C_{1-2}$ alkyl alkoxy sulfate; and
ii) sodium $C_{14}$-$C_{16}$ alkenyl sulfonate;
b) from about 20% to about 40% by weight of one or more $C_{10}$-$C_{16}$ alkyl amide betaine zwitterionic surfactants chosen from {[3-(decanoylamino)-ethyl](dimethyl)ammonio}acetate, {[3-(decanoylamino)ethyl](dimethyl)-ammonio}acetate, {[3-(dodecanoylamino)ethyl](dimethyl)ammonio}-acetate, {[3-(dodecanoylamino)propyl](dimethyl)ammonio}acetate, {[3-(dodecanoylamino)butyl](dimethyl)ammonio}acetate, {[3-(tetradecanoylamino)ethyl](dimethyl)ammonio}acetate, {[3-(tertadecanoylamino)-propyl](dimethyl)ammonio}acetate, {[3-(hexadecanoylamino)ethyl]-(dimethyl)ammonio}acetate, and {[3-(hexadecanoylamino)propyl]-(dimethyl)ammonio}acetate; and
c) from about 1.5% to about 8.5% by weight of a $C_8$-$C_{18}$ alkylglycosidyl nonionic chosen from n-octyl β-D-glucopyranoside, n-decyl β-D-glucopyranoside, n-dodecyl β-D-glucopyranoside, n-tetradecyl β-D-glucopyranoside, n-octyl β-D-maltopyranoside, n-decyl β-D-maltopyranoside, n-dodecyl β-D-maltopyranoside, n-tetradecyl β-D-maltopyranoside, n-octyl β-D-mannopyranoside, n-decyl β-D-mannopyranoside, n-dodecyl β-D-mannopyranoside and n-tetradecyl β-D-mannopyranoside;

B) from about 0.5% to about 15% by weight of a composition modifier system comprising:
a) from about 10% to about 50% by weight of one or more thickeners;
b) from about 25% to about 90% by weight of a foaming agent; and
c) optionally from about 5% to about 15% by weight of one or more aesthetic agents;

C) from about 0.5% to about 10% by weight of a keratin-containing fiber enhancement system comprising:
a) from about 10% to about 50% by weight of one or more emollients and/or humecticants;
b) from about 10% to about 50% by weight of one or more wetting agents;
c) from about 10% to about 50% by weight of one or more antistatic agents; and D) the balance one or more carriers.

Another embodiment of this aspect, the compositions comprise:

A) from about 25% to about 60% by weight of a surfactant system;
B) from about 0.5% to about 15% by weight of a composition modifier system comprising:
a) from about 10% to about 50% by weight of one or more cationic polymeric thickeners;
b) from about 25% to about 90% by weight of a foaming agent chosen from $C_{10}$-$C_{16}$ alkyl monoethanolamines include N-(2-hydroxyethyl)decanamide ($C_{10}$ alkyl monoethanolamine), N-(2-hydroxyethyl)-dodecanamide ($C_{1-2}$ alkyl monoethanolamine, cocamide MEA), and N-(2-hydroxyethyl)tetra-decanamide ($C_{1-6}$ alkyl monoethanolamine); and c) optionally from about 5% to about 15% by weight of an aesthetic and preservative system comprising:
   i) from about 20% to about 70% by weight of one or more preservatives;
   ii) from about 0.01% to about 5% by weight of one or more UV protectants;
   iii) from about 10% to about 50% by weight of one or more pearlizing agents; and
   iv) from about 10% to about 50% by weight of one or more fragrances and colorants;

C) from about 0.5% to about 10% by weight of a keratin-containing fiber enhancement system comprising:
   a) from about 10% to about 50% by weight of one or more emollients and/or humectants;
   b) from about 10% to about 50% by weight of one or more wetting agents; and
   c) from about 10% to about 50% by weight of one or more antistatic agents; and D) the balance one or more carriers.

In a still further embodiment of this aspect, the compositions comprise:

A) from about 25% to about 60% by weight of a surfactant system;
B) from about 0.5% to about 15% by weight of one or more composition modifiers;
C) from about 0.5% to about 10% by weight of a keratin-containing fiber enhancement system comprising:
   a) from about 10% to about 50% by weight of one or more emollients and/or humectants;
   b) from about 10% to about 50% by weight of one or more wetting agents chosen from:
      i) one or more from about 0.5% to about 15% by weight of one or more composition modifiers;
      ii) polyalkyl or polyaryl siloxanes having the following formula:

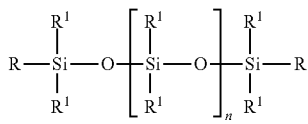

wherein R represents groups which block the ends of the silicone chains, $R^1$ is alkyl or aryl, and the index n is an integer from about 7 to about 8,000;
      iii) and mixtures thereof;
   c) from about 10% to about 50% by weight of an antistatic agent chosen from
i) laurdimonium hydroxyethylcellulose, cocodimonium hydroxyethylcellulose, steardimonium hydroxyethylcellulose and mixtures thereof; and
ii) one or more polyquaternium agents chosen from polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-44, polyquaternium-27 and polyquaternium-55; and D) the balance one or more carriers.

The disclosed compositions comprise one or more optional ingredients, however, the compositions comprise at least one ingredient from any listing of optional ingredients. In addition, any of the herein below recited ingredients can be specifically excluded from any of the disclosed compositions, for example, an individual emollient can be excluded or emollients as a class can be excluded from any of the compositions falling under the disclosure or the compositions, methods or kits recited in the appended claims.

INGREDIENTS

Surfactants

The disclosed restorative hair cleansing, conditioning, and maintenance, conditioning and maintenance compositions comprise from about 25% to about 60% by weight of a surfactant system. In one aspect, the compositions comprise from about 25% to about 50% by weight of a surfactant system. In another aspect, the compositions comprise from about 30% to about 45% by weight of a surfactant system.

Anionic Surfactants

The disclosed restorative hair cleansing, conditioning, and maintenance compositions can comprise one of more anionic surfactants. The following are non-limiting examples of anionic surfactants suitable for use in the disclosed compositions.

1. Alkyl Sulfates

The disclosed compositions can comprise one or more $C_{10}$-$C_{20}$ primary, branched chain and random alkyl sulfates having the formula $ROSO_3M$ wherein R is a linear or branched chain comprising from 10 to 20 carbon atoms and M represents a water soluble cation. Non-limiting examples of alkyl sulfates suitable for use in the disclosed compositions include sodium decylsulfate, sodium dodecylsulfate, sodium tetradecylsulfate, sodium hexadecylsulfate, and sodium octadecylsulfate.

2. Alkyl Alkoxy Sulfates

The disclosed compositions can comprise one or more $C_{10}$-$C_{18}$ alkyl alkoxy sulfates having the formula:

wherein the index x is from 9 to 17, y is from 1 to 7 and M is a water soluble cation chosen from ammonium, lithium, sodium, potassium and mixtures thereof. A non-limiting example includes sodium dodecyl diethoxy sulfate having the formula:

Alkyl alkoxy sulfates are also commercially available as a mixture of ethoxylates, for example, sodium laureth sulfate is available as a mixture of ethoxylates, i.e., the index y is from 2 to 4. Other suitable examples include sodium laureth-2 sulfate having an average of 2 ethoxylates and a $C_{12}$ linear alkyl chain. Sodium laureth-2 is available as Texapon™ N 56 from Cognis Corp. Further examples of alkyl alkoxy sulfates includes sodium laureth-1 sulfate, sodium laureth-3 sulfate, sodium laureth-4 sulfate, sodium myreth-2 sulfate and sodium myreth-3 sulfate.

3. Alkenyl Sulfonates

The disclosed compositions can comprise one or more $C_{10}$-$C_{18}$ alkenyl sulfonates (α-olefin sulfonates) having the formula:

wherein the index z is from 7 to 15 and M is a water soluble cation chosen from ammonium, lithium, sodium, potassium and mixtures thereof. Olefin sulfonates are commercially available as a mixture of alkenyl chains, for example, sodium $C_{14}$-$C_{16}$ olefin sulfonate Bio-Terge™ AS-40 available from Stepan. Further non-limiting examples of alkenyl sulfonates include $C_{12}$-$C_{16}$ olefin sulfonates and $C_{14}$-$C_{18}$ olefin sulfonates. Another example is $C_{12}$-$C_{15}$ pareth-15 sulfonate available as Avanel™ S 150 CG.

4. Alkyl Alkoxy Carboxylates

The disclosed compositions can comprise one or more $C_{10}$-$C_{18}$ alkyl alkoxy carboxylates having the formula:

$$CH_3(CH_2)_x(OCH_2CH_2)_yCO_2M$$

wherein the index x is from 9 to 17, y is from 1 to 5 and M is a water soluble cation chosen from ammonium, lithium, sodium, potassium and mixtures thereof. A non-limiting example includes sodium dodecyl diethoxy carboxylate having the formula:

$$CH_3(CH_2)_{11}(OCH_2CH_2)_2CO_2Na.$$

Alkyl alkoxy carboxylates are also commercially available as a mixture of ethoxylates, for example, sodium laureth sulfate is available as a mixture of ethoxylates, i.e., the index y is from 2 to 4. Other suitable examples include sodium laureth-2 sulfate having an average of 2 ethoxylates and a $C_{12}$ linear alkyl chain. Sodium laureth-2 is available as Texapon™ N 56 from Cognis Corp. Further examples of alkyl alkoxy sulfates include sodium laureth-1 sulfate, sodium laureth-3 sulfate, sodium laureth-4 sulfate, sodium myreth-2 sulfate and sodium myreth-3 sulfate.

5. Isethionate Esters of Alkyl Alkoxy Carboxylic Acids

The disclosed compositions can comprise one or more $C_{10}$-$C_{18}$ isethionate esters of alkyl alkoxy carboxylates having the formula:

$$CH_3(CH_2)_x(OCH_2CH_2)_yOCH_2C(O)OCH_2CH_2SO_3M$$

wherein the index x is from 9 to 17, the index y is from 1 to 5 and M is a water soluble cation. Isethionate esters of alkyl alkoxy carboxylates are described in U.S. Pat. No. 5,466,396 the disclosure of which is included herein by reference in its entirety.

6. Alkyl Carboxyamides

The disclosed compositions can comprise one or more $C_{10}$-$C_{18}$ alkyl carboxyamides having the formula:

$$CH_3(CH_2)_xC(O)NR(CH_2)_yCO_2M$$

wherein R is hydrogen or methyl the index x is from 9 to 17, the index y is from 1 to 5 and M is a water soluble cation. A non-limiting example of an alkyl carboxyamide suitable for use in the disclosed compositions includes potassium cocoyl glycinate available as AMILITE™ GCK-12 from Ajinomoto. A further example includes compounds wherein R is methyl, for example, sodium cocoyl sarcosinate.

Zwitterionic Surfactants

The disclosed restorative hair cleansing, conditioning, and maintenance compositions can comprise from about 5% to about 25% by weight of one of more zwitterionic (amphoteric) surfactants. The following are non-limiting examples of zwitterionic surfactants suitable for use in the disclosed compositions.

1. Alkyl Amide Betaines

One category of zwitterionic surfactants relates to $C_{10}$-$C_{16}$ alkyl amide betaines having the formula:

$$CH_3(CH_2)_wC(O)NH(CH_2)_uN^+(CH_3)_2(CH_2)_tCO_2^-$$

wherein the index w is from 9 to 15, the index u is from 1 to 5 and the index t is from 1 to 5. Non-limiting examples of betaine surfactants includes {[3-(decanoylamino)ethyl]-(dimethyl)-ammonio}acetate, {[3-(decanoyl)ethyl](dimethyl)ammonio}-acetate, {[3-(dodecanoyl-amino)ethyl](dimethyl)ammonio}acetate, {[3-(dodecanoylamino)propyl]-(dimethyl)-ammonio}acetate, {[3-(dodecanoylamino)-butyl](dimethyl)ammonio}acetate, {[3-(tetra-decanoylamino)ethyl](dimethyl)-ammonio}acetate, {[3-(tertadecanoylamino)-propyl](dimethyl) ammonio}acetate, {[3-(hexadecanoylamino)ethyl](dimethyl)-ammonio}acetate, and {[3-(hexa-decanoylamino)propyl](dimethyl)ammonio}acetate.

2. Alkyl Amide Sultaines

Another category of zwitterionic surfactants relates to $C_{10}$-$C_{16}$ alkyl amide sultaines having the formula:

$$CH_3(CH_2)_wC(O)NH(CH_2)_uN^+(CH_3)_2(CH_2)_tSO_3^-$$

wherein the index w is from 9 to 15, the index u is from 1 to 5 and the index t is from 1 to 5. Non-limiting examples of sultaine surfactants includes {[3-(decanoylamino)ethyl]-(dimethyl)-ammonio}methanesulfonate, {[3-(decanoylamino)ethyl](dimethyl)ammonio}-methanesulfonate, {[3-(dodecanoyl-amino)ethyl](dimethyl) ammonio}methanesulfonate, {[3-(dodecanoylamino)-propyl](dimethyl)ammonio}methanesulfonate, {[3-(dodecanoyl-amino)butyl](dimethyl)-ammonio}methanesulfonate, {[3-(tetradecanoylamino) ethyl]-(dimethyl)ammonio}methane-sulfonate, {[3-(tertadecanoylamino)propyl](dimethyl)-ammonio}methanesulfonate, {[3-(hexadecanoylamino) ethyl](dimethyl)ammonio}-methanesulfonate, and {[3-(hexadecanoylamino)propyl](dimethyl)ammonio}-methanesulfonate.

3. Alkyl Hydroxy Sultaines

A further category of zwitterionic surfactants relates to $C_{10}$-$C_{16}$ alkyl hydroxy sultaines having the formula:

$$CH_3(CH_2)_wN^+(CH_3)_2CH_2CHOHCH_2SO_3^-$$

wherein the index w is from 9 to 15. Non-limiting examples of alkyl hydroxy sultaine surfactants includes 3-[dodecyl(dimethyl)azaniumyl]-2-hydroxypropane-1-sulfonate (lauryl hydroxysultaine), 3-[tetradecyl(dimethyl)azaniumyl]-2-hydroxypropane-1-sulfonate (myristyl hydroxysultaine), (Z)-{dimethyl[3-(octadec9-enamido)propyl]ammonio}-methanesulfonate (oleyl hydroxysultaine), and the like.

Nonionic Surfactants

The disclosed restorative hair cleansing, conditioning, and maintenance compositions can comprise one of more non-ionic surfactants. The following are non-limiting examples of nonionic surfactants suitable for use in the disclosed compositions.

1. Alkyl Glucosides

One category of nonionic surfactants relates to $C_8$-$C_{18}$ alkylglycosidyl nonionic surfactant having the formula:

$$CH_3(CH_2)_qO[G]_pH$$

wherein G represents a monosaccharide residue chosen from glucose, fructose, mannose, galactose, talose, allose, altrose, idose, arabinose, xylose, lyxose, ribose and mixtures thereof, the index p is from 1 to 4, the index q is from 7 to 17. The following are non-limiting examples of alkyl glucoside surfactants include (2R,3S,4S,5R,6R)-2-(hydroxymethyl)-6-octooxyoxane-3,4,5-triol (octyl glucoside, n-octyl-β-D-glucoside), (2R,3R,4S,5S,6R)-2-decoxy-6-(hydroxymethyl)tetrahydropyran-3,4,5-triol(decyl glucoside, n-decyl-β-D-glucoside), and (2R,3R,4S,5S,6R)-2-dodecoxy-6-(hydroxymethyl)tetrahydropyran-3,4,5-triol (dodecyl glucoside, lauryl glucoside, n-dodecyl-β-D-glucoside). One example of a suitable admixture of $C_8$-$C_{16}$ alkylglycosidyl nonionic surfactants is PLANTACARE™ 818 UP available from Cogins Chemical Co.

2. Polyoxyethylene Glycol Alkyl Ethers

A further category of nonionic surfactants relates to polyoxyethylene glycol alkyl ethers having the formula:

$$RO(CH_2CH_2O)_nH$$

wherein R is a linear or branched alkyl group having from 6 to 20 carbon atoms and n is an integer of about 2 to about 20.

On example of suitable ethoxylate alcohol surfactants are the NEODOL™ ethoxylated alcohols from Shell Chemicals. NEODOL™ 23-1 is a surfactant comprising a mixture of R units that are $C_{12}$ and $C_{13}$ in length with an average of 1 ethoxy unit. Non-limiting examples of ethoxylated alcohols include NEODOL™ 23-1, NEODOL™ 23-2, NEODOL™ 23-6.5, NEODOL™ 25-3, NEODOL™ 25-5, NEODOL™ 25-7, NEODOL™ 25-9, PLURONIC™ 12R3, and PLURONIC™ 25R2 available from BASF.

3. Polyoxypropylene Glycol Alkyl Ethers

A still further category of nonionic surfactants relates to polyoxyethylene glycol alkyl ethers having the formula:

$$RO(CH_2CH(CH_3)O)_nH$$

wherein R is a linear or branched alkyl group having from 6 to 20 carbon atoms and n is an integer of about 2 to about 20.

4. Polyoxyethylene Polyoxypropylene Block Copolymers

Another category of nonionic surfactants suitable for use in the disclosed compositions includes polyoxyethylene polyoxypropylene block copolymers known as "poloxamers" having the formula:

$$HO(CH_2CH_2)_{y1}(CH_2CH_2CH_2O)_{y2}(CH_2CH_2O)_{y3}OH$$

these are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol. These extracellular desiccants are also well known by the trade name PLURONICS™. These compounds are commonly named with the word Poloxamer followed by a number to indicate the specific co-polymer, for example Poloxamer 407 having two PEG blocks of about 101 units ($y^1$ and $y^3$ each equal to 101) and a polypropylene block of about 56 units. This category of nonionic surfactant is commercially, for example, under the trade name LUTROL™ F-17 available from BASF.

5. Alkoxylated Alkyl Amides

A yet still further category of nonionic surfactants suitable for use in the disclosed compositions includes alkyl amides that are ethoxylate, propoxylated, or mixtures thereof, having the formula:

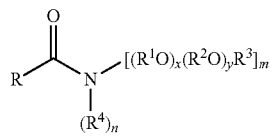

wherein R is $C_7$-$C_{21}$ linear alkyl, $C_7$-$C_{21}$ branched alkyl, $C_7$-$C_{21}$ linear alkenyl, $C_7$-$C_{21}$ branched alkenyl, and mixtures thereof. $R^1$ is ethylene; $R^2$ is $C_3$-$C_4$ linear alkylene, $C_3$-$C_4$ branched alkylene, and mixtures thereof; in some iterations $R^2$ is 1,2-propylene. Nonionic surfactants that comprise a mixture of $R^1$ and $R^2$ units can comprise from about 4 to about 12 ethylene units in combination with from about 1 to about 4 1,2-propylene units. The units can be alternating or grouped together in any combination suitable to the formulator. In one iteration, the ratio of $R^1$ units to $R^2$ units is from about 4:1 to about 8:1. In another iteration, a $R^2$ unit (i.e., 1,2-propylene) is attached to the nitrogen atom followed by the balance of the chain comprising from 4 to 8 ethylene units.

$R^3$ is hydrogen, $C_1$-$C_4$ linear alkyl, $C_3$-$C_4$ branched alkyl, and mixtures thereof; preferably hydrogen or methyl, more preferably hydrogen.

$R^4$ is hydrogen, $C_1$-$C_4$ linear alkyl, $C_3$-$C_4$ branched alkyl, and mixtures thereof. When the index m is equal to 2 the index n must be equal to 0 and the $R^4$ unit is absent and is instead replaced by a —$[(R^1O)_x(R^2O)_yR^3]$ unit.

The index m is 1 or 2, the index n is 0 or 1, provided that when m is equal to 1, n is equal to 1; and when m is 2 n is 0; in one example, m is equal to 1 and n is equal to one, resulting in one —$[(R^{1O})_x(R^{2O})_yR^3]$ unit and $R^4$ being present on the nitrogen. The index x is from 0 to about 50, in one embodiment from about 3 to about 25, in another embodiment x is from about 3 to about 10. The index y is from 0 to about 10, in one example y is 0; however, when the index y is not equal to 0, y is from 1 to about 4. In one embodiment all of the alkyleneoxy units are ethyleneoxy units.

Another category of surfactants suitable for use in the disclosed compositions include the bis(3-alkoxypropan-2-ol) sulfides, sulfoxides and sulfones as disclosed in U.S. Pat. No. 7,476,766, the disclosure of which is included herein by reference in its entirety.

Foaming Agents

The disclosed restorative hair cleansing, conditioning, and maintenance compositions can comprise from about 0.5% to about 10% by weight of one or more foaming agents. Foaming agents are also referred to as structurants by the artisan although the compounds themselves can have surfactant properties, for example, the disclosed foaming agents can be considered by the artisan in some embodiments to be nonionic surfactants. The following are non-limiting examples of categories of foaming agents:

i) alkanolamides, for example, cocamide MEA, cocamide DEA and Cocamide MIPA;
ii) $C_8$-$C_{24}$ linear or branched fatty acids, for example, dodecanoic acid (lauric acid), tetradecanoic acid (myristic acid), and the like;
iii) $C_8$-$C_{24}$ linear or branched fatty acid esters, for example, methyl dodecanoate (methyl laurate), methyl tetradecanoate (methyl myristate), and the like;
iv) $C_{10}$-$C_{24}$ linear alcohols or $C_{10}$-$C_{24}$ ethoxylated and/or propoxylated linear alcohols, for example, dodecanol, tetradecanol, laureth-2, laureth-3, laureth-4, and the like.

In one aspect the compositions comprise from about 1.5% to about 5% by weight of a $C_{10}$-$C_{16}$ alkyl monoethanolamine Non-limiting examples of $C_{10}$-$C_{16}$ alkyl monoethanolamines include N-(2-hydroxyethyl)decanamide ($C_{10}$ alkyl monoethanolamine), N-(2-hydroxyethyl)-dodecanamide ($C_{1-2}$ alkyl monoethanolamine, cocamide MEA), and N-(2-hydroxyethyl)tetra-decanamide ($C_{1-6}$ alkyl monoethanolamine).

In another aspect the compositions comprise from about 1.5% to about 5% by weight of a $C_{10}$-$C_{16}$ alkyl diethanolamine. Non-limiting examples of $C_{10}$-$C_{16}$ alkyl diethanolamines include N,N-bis(2-hydroxyethyl)decanamide ($C_{10}$ alkyl diethanolamine), N,N-bis(2-hydroxyethyl)-dodecanamide ($C_{1-2}$ alkyl diethanolamine, cocamide DEA), and N,N-bis(2-hydroxyethyl)tetra-decanamide ($C_{1-6}$ alkyl diethanolamine)

Wetting Agents

The disclosed restorative hair, conditioning, and maintenance can comprise from about 0.1% to about 20% by weight of one or more silicone comprising polymers. In one embodiment, the compositions can comprise from about 0.15% to about 10% by weight of one or more silicone polymers. In another embodiment, the compositions can comprise from about 0.2% to about 8% by weight of one or more silicone polymers. In a still further embodiment, the compositions can comprise from about 0.1% to about 3% by weight of one or mere wetting agents.

Typically the silicone compounds useful herein, as a single compound, as a blend or admixture of at least two silicone compounds, or as a blend or admixture of at least one silicone compound and at least one solvent, have a viscosity of from about 1,000 to about 2,000,000 mPas at 25° C. As such, the viscosity can be measured by means of a glass capillary viscometer as set forth in Dow Corning Corporate Test Method CTM0004, Jul. 20, 1970. Non-limiting examples of suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having keratin-containing fibers restorative and/or conditioning properties can also be used.

One non-limiting example of silicone compounds that can comprise the disclosed compositions includes polyalkyl or polyaryl siloxanes having the following formula:

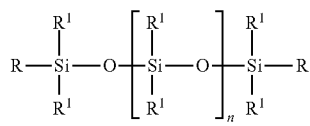

wherein $R^1$ is alkyl or aryl, and the index n is an integer from about 7 to about 8,000. R represents groups which block the ends of the silicone chains. The alkyl or aryl groups substituted on the siloxane chain ($R^1$) or at the ends of the siloxane chains R can have any structure as long as the resulting silicone remains fluid at room temperature, is dispersible, is neither irritating, toxic nor otherwise harmful when applied to the keratin-containing fibers, is compatible with the other components of the composition, is chemically stable under normal use and storage conditions, and is capable of being deposited on and conditions the keratin-containing fibers. In one embodiment, R groups include hydroxy, methyl, methoxy, ethoxy, propoxy, and aryloxy. The two $R^1$ groups on the silicon atom may represent the same group or different groups. In one embodiment, the two $R^1$ groups represent the same group. Non-limiting examples of $R^1$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known to the artisan as dimethicone, and derivatives thereof, are one embodiment of the disclosed silicones. The polyalkylsiloxanes that can be used include, for example, polydimethylsiloxanes. These silicone compounds are available, for example, from the General Electric Company in their Viscasil™ and TSF 451 series, and from Dow Corning in their Dow Corning SH200 series.

The herein disclosed polyalkylsiloxanes are available, for example, as an admixture with silicone compounds having a lower viscosity. Such admixtures have a viscosity of from about 1,000 mPas to about 100,000 mPas. In another example, from about 5,000 mPas to about 50,000 mPas. Such admixtures can comprise:
 i) a first silicone having a viscosity of from about 100,000 mPas to about 30,000,000 mPas at 25° C.; and
 ii) a second silicone having a viscosity of from about 5 mPas to about 10,000 mPas at 25° C.
In a further example, the silicone admixture can comprise:
 i) a first silicone having a viscosity of from about 100,000 mPas to about 20,000,000 mPas at 25° C.; and
 ii) a second silicone having a viscosity of from about 5 mPas to about 5,000 mPas at 25° C.

Admixtures that can be included in the disclosed compositions are, for example, a blend of dimethicone having a viscosity of 18,000,000 mPas and dimethicone having a viscosity of 200 mPas available from GE Toshiba, and a blend of dimethicone having a viscosity of 18,000,000 mPas and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Non-limiting examples include polydimethylsiloxane, poly(dimethylsiloxane methylvinylsiloxane) copolymer, poly(dimethylsiloxane diphenylsiloxane methylvinylsiloxane) copolymer and mixtures thereof. Silicone gums are available, for example, as an admixture with silicone compounds having a lower viscosity. Such mixtures useful herein include, for example, Gum/Cyclomethicone blend available from Shin-Etsu.

The silicone compounds that can be used include, for example, a polypropylene oxide modified polydimethylsiloxane although ethylene oxide or mixtures of ethylene oxide and propylene oxide can also be used. The ethylene oxide and polypropylene oxide level should be sufficiently low so as not to interfere with the dispersibility, wetting, or humectants properties of the silicone. These materials are also known to the artisan as dimethicone copolyols.

One example of silicones that can be used as wetting agents includes from about 0.5% to about 15% by weight of one or more composition modifiers such as PEG-12 Dimethicone sold as D.C. Surfactant™ 193C by Dow Chemical. Other wetting agents include ethyleneoxide modified polydimethyl siloxanes, for example, SILSENSE™ Copolyol-1 and SCHERCOMID™ AME-100 available from Noveon Consumer Specialties and vegetable derived polyesters, for example, PELEMOL™ PHS-8 available from Phoenix Chemical, Inc.

Emollients and Humectants

The disclosed restorative hair, conditioning, and maintenance compositions can comprise from about 0.1% to about 10% by weight of one or more emollients and/or humectants.

One example of a emollient suitable for use in a disclosed conditioning composition is 2-hydroxy-N-(2-hydroxyethyl) propanamide (lactamide MEA) available as Mackamide™ LME from Mcintyre. The conditioning compositions can comprise from about 0.01% to about 5% by weight of lactamide MEA. In one embodiment, the compositions comprise from about 0.3% to about 0.7% by weight of lactamide MEA.

The disclosed compositions can comprise from about 0.1% to about 3% by weight of one or more emollients. Non-limiting examples of emollients include but are not limited to $C_{14}$-$C_{22}$ fatty alcohols, for example, cetyl alcohol, stearyl alcohol, cetearyl alcohol; $C_{14}$-$C_{22}$ fatty alcohols fatty acid esters, for example, isopropyl mysristate, isopropyl palmitate, diisopropyl dimer dilinoleate; $C_8$-$C_{14}$ fatty alcohol triglycerides, for example, caprylic/capric triglyceride; cetyl esters; $C_8$-$C_{40}$ hydrocarbons, for example, light mineral oil, white petrolatum; and waxes, for example, beeswax. Mixtures of one or more classes of emollients can also comprise the disclosed compositions, for example, a mixture of $C_{14}$-$C_{22}$ fatty alcohols and $C_{14}$-$C_{22}$ fatty alcohols fatty acid esters.

A further embodiment of emollients relates to partial esters of natural oils in combination with silicone, for example, the triglyceride extracted from *Limnathes alba* (Meadowfoam Seed) is partially esterified with polyethylene glycol. One example of an emollient of this embodiment includes dimethicone PEG-8 meadowfoamate Emulsifiers The disclosed compositions can further comprise from about 5% to about 25% by weight of one or more emulsifiers.

Non-limiting examples of emulsifiers include $C_{14}$-$C_{22}$ fatty alcohols chosen from 1-tetradecanol (myristyl alcohol), 1-hexadecanol (cetyl alcohol), cis-9-hexadecen-1-ol (plamitoleyl alcohol), 1-octadecanol (stearyl alcohol), cis-9-octadecen-1-ol (oleyl alcohol), trans-9-octadecen-1-ol (elaidyl alcohol), 1-eicosanol (arachidyl alcohol), and 1-docosanol (behenyl alcohol). Further non-limiting examples of emulsifiers include esters of $C_{14}$-$C_{22}$ fatty alcohols and inorganic acids chosen from di-1-tetradecanyl phosphate (di-myristyl phosphate), di-1-hexadecanyl phosphate (di-cetyl phosphate), di-cis-9-hexadecen-1-yl phosphate (di-plamitoleyl phosphate), di-1-octadecanyl phosphate (di-stearyl phosphate), di-cis-9-octadecen-1-yl phosphate (di-oleyl phosphate), di-trans-9-octadecen-1-yl phosphate (di-elaidyl phosphate), di-1-eicosanyl phosphate (di-arachidyl phosphate), di-1-docosanyl phosphate (di-behenyl phosphate), 1-tetradecanyl sulfate (myristyl sulfate), 1-hexadecanyl sulfate (cetyl sulfate), cis-9-hexadecen-1-yl sulfate (plamitoleyl sulfate), 1-octadecanyl sulfate (stearyl sulfate), cis-9-octadecen-1-yl sulfate (oleyl sulfate), trans-9-octadecen-1-yl sulfate (elaidyl sulfate), 1-eicosanyl sulfate (arachidyl sulfate), and 1-docosanyl sulfate (behenyl sulfate).

Yet further non-limiting examples of emulsifiers include ethers of polyoxyethylene, polyoxypropylene, and polyoxyethylene/polyoxypropylene and inorganic acids or ethers of $C_{14}$-$C_{22}$ fatty alcohols chosen from PPG-5-Ceteth-20 phosphate, Ceteth-10 phosphate, Ceteth-10, and Ceteareth-20. Still further non-limiting examples of emulsifiers includes non-ionic surfactants, for example, polysorbate 60, sorbitan monostearate, polyglyceryl-4 oleate, polyoxyethylene(4) lauryl ether, and the like. In certain embodiments, the emulsifier is chosen from poloxamers (e.g., PLURONIC™ F68, also known as POLOXAMER™ 188, a poly(ethylene glycol)-block-poly(propylene glycol)-block-poly(ethylene glycol), available from BASF, Ludwigshafen, Germany) and sorbitan trioleate (e.g., SPAN™ 85 available from Uniqema, New Castle, Del.).

Viscosity Control Agents

The disclosed compositions can comprises from about 2% to about 7% by weight of one or more viscosity control agents. The formulations of the present invention can also comprise a viscosity-enhancing agent. Examples of suitable viscosity enhancing agents include long chain alcohols, for example, cetyl alcohol, stearyl alcohol, cetearyl alcohol; cellulose ethers such as hydroxypropylmethylcellulose, hydroxyethylcellulose, hydroxypropylcellulose, and carboxymethylcellulose; polysaccharide gums such as xanthan gum; and homopolymers and copolymers of acrylic acid crosslinked with allyl sucrose or allyl pentaerythriol such as those polymers designated as carbomers in the United States Pharmacopoeia. Suitable carbomers include, for example, those available as CARBOPOL™ 934P, CARBOPOL™ 971P, CARBOPOL™ 940, CARBOPOL™ 974P, CAR-BOPOL™ 980, and PEMULEN™ TR-1 (USP/NF Monograph; Carbomer 1342), all available from Noveon, Cleveland, Ohio.

The compositions can contain one or more thickeners that assist in maintaining an increased viscosity of the final composition. Suitable thickeners are those set forth above with respect to the oxidative composition, and in the same ranges. Also suitable are a variety of water soluble anionic thickening polymers such as those disclosed in U.S. Pat. No. 4,240,450, which is hereby incorporated by reference in its entirety. In one aspect, the activator compositions comprise from about 0.01% to about 5% by weight of a thickener useful as a viscosity control agent. In one embodiment the activator composition comprises from about 0.05% to about 4% by weight of a thickener useful as a viscosity control agent. In a further embodiment the activator composition comprises from about 0.1% to about 3% by weight of a thickener useful as a viscosity control agent. Examples of such anionic polymers are copolymers of vinyl acetate and crotonic acid, graft copolymers of vinyl esters or acrylic or methacrylic acid esters, cross-linked graft copolymers resulting from the polymerization of at least one monomer of the ionic type, at least one monomer of the nonionic type, polyethylene glycol, and a crosslinking agent, and the like. Preferred are acrylate copolymers such as steareth-10 alkyl ether acrylate copolymer.

Thickening Polymer

The disclosed restorative hair cleansing, conditioning, and maintenance compositions can comprise from about 0.05% to about 5% by weight of one or more thickeners. In one embodiment, the compositions comprise from about 0.05% to about 2% by weight of one or more thickeners. In another embodiment, the compositions comprise from about 0.1% to about 0.5% by weight of one or more thickeners.

In general, one category of thickening polymers useful herein are those which can provide the composition with an appropriate viscosity of from about 1,000 cps to about 50,000 cps. In another embodiment, the viscosity is from about 5,000 cps to about 40,000 cps. In a further embodiment, the viscosity is from about 10,000 cps to about 30,000 cps. The viscosity is conveniently measured at 25° C. utilizing a Brookfield Viscometer at shear rate of 1.0 rpm.

A variety of thickening polymers can be used in the disclosed compositions. Non-limiting examples of thickening polymers useful herein include, for example, cellulose and its derivatives such as cellulose ethers, hydrophobically modified cellulose ethers, and quaternized celluloses; nonionic guar gums; cationic guar gums; crosslinked polymers such as nonionic crosslinked polymers and cationic crosslinked polymers; and acrylate polymers such as sodium polyacrylate, polyethylacrylate, and polyacrylamide. The thickening polymers useful herein may include the polymers disclosed below under the title "CATIONIC POLYMER". Among a variety of thickening polymers, preferred are nonionic guar gums.

A cationic guar polymer useful herein can have a molecular weight of from about 100,000 AMU (Atomic Mass Unit) to about 4,000,000 AMU. In another embodiment, a cationic guar polymer useful herein can have a molecular weight of from about 500,000 AMU to about 3,500,000 AMU. In a further embodiment, a cationic guar polymer useful herein can have a molecular weight of from about 1,000,000 AMU to about 3,000,000 AMU. In a yet further embodiment, a cationic guar polymer useful herein can have a molecular weight of from about 1,600,000 AMU to about 2,800,000 AMU. One example of a commercially available cationic thickener is Jaguar™ C-14S available from Rhodia.

A nonionic guar polymer useful herein can have a molecular weight of from about 100,000 AMU (Atomic Mass Unit) to about 4,000,000 AMU. In another embodiment, a nonionic guar polymer useful herein can have a molecular weight of from about 500,000 AMU to about 3,500,000 AMU. In a further embodiment, a nonionic guar polymer useful herein can have a molecular weight of from about 1,000,000 AMU to about 3,000,000 AMU. In a yet further embodiment, a nonionic guar polymer useful herein can have a molecular weight of from about 1,600,000 AMU to about 2,800,000 AMU. One example of a commercially available cationic thickener is Jaguar™ HP-105 available from Rhodia.

Further examples of useful thickening agents include, but are not limited to, any of the various cellulosic ethers known in the art, for example, a hydroxyethyl cellulose thickener such as Cellosize™ PCG-10 available from Dow Chemical. In addition, a hydroxyethyl cellulose sodium acetate can be used, for example Cellosize™ 52000H available from Dow Chemical. Further examples of thickeners that can be used include carboxypolymethylene, polyethylene oxide, polyacrylic acids, copolymers of polyacrylic acid, polyacrylates, polyacrylamides, copolymers of polyacrylic acid and polyacrylamide, polyvinylpyrrolidone (PVP), PVP-vinyl acetate copolymers, carboxymethylcellulose, carboxypropylcellulose, polysaccharide gums, and proteins.

The one or more thickening agents may be added in order to alter the rheology or consistency of the composition so that it can be applied more evenly, while reducing or eliminating waste. The thickening agent can increase the viscosity of the composition and results in a composition having the consistency of a cream or lotion that more easily stays where placed. In the absence of a thickening agent, the hair restorative composition is more fluid, having a consistency more similar to water, which can make it difficult to apply evenly throughout the damaged hair without requiring a large excess. Applying a large excess of particularly as the composition begins to stiffen or solidify during the hair restoration process.

Antistatic Agents

The disclosed restorative hair, conditioning, and maintenance compositions can comprise from about 0.05% to about 5% by weight of one or more antistatic agents. In one embodiment, the compositions comprise from about 0.05% to about 2% by weight of one or more antistatic agents. In another embodiment, the compositions comprise from about 0.1% to about 0.5% by weight of one or more antistatic agents.

One example of an antistatic agent that can be used to provide treated keratin-containing fibers with non-clumping or non-tangling properties making wet and dry combing easier are the quaternary cellulose polymers wherein their quaternary structure contains $C_{10}$-$C_{22}$ linear alkyl units. Non-limiting examples include PG-hydroxyethyl cellulose laurdiammonium chloride (laurdimonium hydroxyethylcellulose, Crodacel™ QL) available from Croda, PG-hydroxyethyl cellulose cocodiammonium chloride (cocodimonium hydroxyethylcellulose, Crodacel™ QL) available from Croda, and PG-hydroxyethyl cellulose steardiammonium chloride (steardimonium hydroxyethylcellulose, Crodacel™ QL) available from Croda, each having an average molecular weight of approximately 100,000 AMU. These antistatic agents are characterized as having an average of 1.2 moles of alkyl quaternary groups per anhydro glucose units.

Further non-limiting examples of synthetic or nonsynthetic cationic polymers that can act as antistatic conditioning agents are polyquaternium agents, for example, polyquaternium-1, polyquaternium-2, polyquaternium-4, polyquaternium-5, polyquaternium-6 (also known as Merquat™ 1000 available from Nalco), polyquaternium-7 (also known as Merquat™ 5500 available from Nalco), polyquaternium-8, polyquaternium-9, polyquaternium-10 (also known as Polymer JR™ 400, sold by Amerchol), polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22 (also known as Merquat™ 280, 281 and 298 available from Nalco), polyquaternium-24, polyquaternium-27, polyquaternium-28, polyquaternium-29 (also known as Kytamer™ KCO available from Amerchol), polyquaternium-30, polyquaternium-31, polyquaternium-32, polyquaternium-33, polyquaternium-34, polyquaternium-35, polyquaternium-36, polyquaternium-37, polyquaternium-39 (also known as Merquat™ 3300 and 3331 available from Nalco), polyquaternium-44, polyquaternium-27 (also known as Merquat™ 2001 available from Nalco) and polyquaternium-55.

Detangling Agent

The disclosed restorative cleansing or conditioning compositions can comprise one or more detangling agents chosen from $C_{10}$-$C_{22}$ alkyl esters of alkoxylated trimethylolpropane, $C_{10}$-$C_{22}$ alkenyl mono-ene esters of alkoxylated trimethylolpropane, $C_{10}$-$C_{22}$ alkynyl mono-yne esters of alkoxylated trimethylolpropane, and mixtures thereof can have the formula:

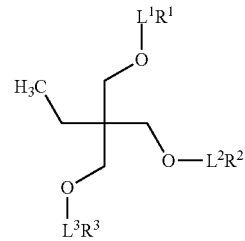

wherein $R^1$, $R^2$ and $R^3$ are each independently chosen from:
  i) hydrogen;
  ii) $C_{10}$-$C_{22}$ carboxyalkyl;
  iii) $C_{10}$-$C_{22}$ carboxyalkenyl; and
  iv) $C_{10}$-$C_{22}$ carboxyalkynyl;

$L^1$, $L^2$ and $L^3$ are linking units each independently chosen from:
  i) —$(CR^{4a}R^{4b})_w$O—; and
  ii) —$[(CR^{5a}R^{5b})_w]_x[O(CR^{6a}R^{6b})_y]_z$O—;

the index w is from 2 to 150, the index x is from 1 to 50, the index y is from 3 to 300, the index z is from 1 to 20; and $R^{4a}$, $R^{4b}$, $R^{5a}$, $R^{5b}$, $R^{6a}$, and $R^{6b}$ are each independently chosen from:
  i) hydrogen; and
  ii) methyl.

The $R^1$, $R^2$ and $R^3$ units comprise $C_{10}$-$C_{22}$ fatty acid residues of the corresponding $C_{10}$-$C_{22}$ fatty acids. In a one aspect of the disclosed detangling agents, $R^1$, $R^2$ and $R^3$ are from 90% to about 99.9% by weight of a single $C_{10}$-$C_{22}$ carboxyalkenyl units. Non-limiting examples of $R^1$, $R^2$ and $R^3$ according to this aspect include the following cis-D carboxyalkenyl residues:
  i) —C(O)(CH)$_7$CH═CH(CH$_2$)$_3$CH$_3$ (myristoleoyl);
  ii) —C(O)(CH)$_7$CH═CH(CH$_2$)$_5$CH$_3$ (palmitoleoyl);
  iii) —C(O)(CH)$_4$CH═CH(CH$_2$)$_8$CH$_3$ (sapienoyl);
  iv) —C(O)(CH)$_7$CH═CH(CH$_2$)$_7$CH$_3$ (oleoyl);
  v) —C(O)(CH)$_7$CH═CHCH$_2$(CH$_2$)$_4$CH$_3$ (linoleoyl); and
  vi) —C(O)(CH)$_{11}$CH═CH(CH$_2$)$_7$CH$_3$ (erucoyl).

In another aspect of the disclosed detangling agents, $R^1$, $R^2$ and $R^3$ are from 90% to about 99.9% by weight of a mixture of $C_{10}$-$C_{22}$ carboxyalkenyl units. Non-limiting examples of $R^1$, $R^2$ and $R^3$ according to this aspect include the following cis-D carboxyalkenyl residues:

i) —C(O)(CH)$_7$CH=CH(CH$_2$)$_3$CH$_3$ (myristoleoyl);
ii) —C(O)(CH)$_7$CH=CH(CH$_2$)$_5$CH$_3$ (palmitoleoyl);
iii) —C(O)(CH)$_4$CH=CH(CH$_2$)$_8$CH$_3$ (sapienoyl);
iv) —C(O)(CH)$_7$CH=CH(CH$_2$)$_7$CH$_3$ (oleoyl);
v) —C(O)(CH)$_7$CH=CHCH$_2$(CH$_2$)$_4$CH$_3$ (linoleoyl); and
vi) —C(O)(CH)$_{11}$CH=CH(CH$_2$)$_7$CH$_3$ (erucoyl).

The first aspect of $L^1$, $L^2$ and $L^3$ relates to linking units that comprise polyoxyethylene polyoxypropylene residues that are derived from the random co-polymerization of ethylene oxide and propylene oxide. The $L^1$, $L^2$ and $L^3$ units can be attached to the central trimethylolpropane core by either grafting the $L^1$, $L^2$ and $L^3$ units onto the trimethylolpropane core or by reacting a polyoxyethylene polyoxypropylene precursor with the trimethylolpropane core.

A one embodiment of this aspect includes a detangling agent wherein each of $L^1$, $L^2$ and $L^3$ comprises greater than about 90% by weight of a polyoxyethylene polyoxypropylene residue comprising about 120 polyoxyethylene and 10 polyoxypropylene units (PEF/PPG 120/10) represented by the formula:

—[(CH$_2$CH$_2$)]$_{120}$[O(CH$_2$CH$_2$)$_3$]$_{10}$O—.

Non-limiting examples of detangling agents according to this embodiment include PEG/PPG-120/10 trimethylolpropane trioleate (and) laureth-2 [CAS Reg. No. 37339-03-0] available as an admixture with ethoxylated lauryl alcohol from Cognis as Arylpon™ TT.

UV Radiation Absorbers

The disclosed compositions can comprise from about 0.005% to 0.05% by weight of one or more UV absorbers. This includes the disclosed restorative cleansing or conditioning systems, as well as the disclosed activator compositions. In one aspect the compositions comprise from about 0.01% to about 0.04% by weight of one or more UV absorbers. The following are non-limiting examples of UV absorbers ethylhexyl methoxycinnamate (octyl methoxycinnamate), methoxydibenzoylmethane (i.e., Parsol™ 1789, Eusolex™ 9020 and Escalol™ 517), polyoxypropylene, polyoxyethylene ethers of aliphatic alcohols (for example, PPG-26 Buteth-26), ethylhexyl salicylate, and polyoxyethylene derivatives of hydroxy fatty acid containing fats and oils, (for example, PEG-40 hydrogenated castor oil). One UV protectant suitable for use is Coabsorb™ EW which comprises an admixture of ethylhexyl methoxycinnamate, butyl methoxydibenzoyl methane, PPG-26-buteth-26, ethylhexyl salicylate, PEG-40-hydrogenated castor oil available from Sensient/LCW Conditioning Agents Keratin-containing fibers can become dry and brittle due to exposure to UV radiation, chemicals used for cleaning the fibers, and from the wearing of apparel. In one embodiment, the disclosed compositions can comprise from about 0.1% to about 1.5% by weight of one or more conditioning agents.

The conditioning agents can comprise polymeric materials or small naturally occurring molecules that interact with the keratin-containing fiber to provide a benefit to the properties of the fibers. In one aspect, the disclosed compositions comprise one or more nonionic amphiphilic homopolymers or copolymers. In one embodiment, the compositions comprise polyalkylene glycols having the formula:

HO(CH$_2$CH$_2$O)$_x$H wherein the index x represent the average number of ethyleneoxy units in the glycol polymer. The index x can be represented by a whole number or a fraction. For example, a polyethylene glycol having an average molecular weight of 8,000 g/mole (PEG 8000) can be equally represented by the formulae:

HO(CH$_2$CH$_2$O)$_{181}$H or HO(CH$_2$CH$_2$O)$_{181.4}$H or the polyethylene glycol can be represented by the common short hand notation: PEG 8000. This notation, common to the artisan is used interchangeably throughout the specification to indicate polyethylene glycols and their average molecular weight. The formulator will understand that depending upon the source of the polyethylene glycol, the range of molecular weights found within a particular sample or lot can range over more or less values of x. For example, one source of PEG 8000 can include polymers wherein the value of x can be from about 175 to about 187, whereas another source can report the range of molecular weights such that x can be from about 177 to about 184. In fact, the formulator, depending upon the condition of the user's keratin-containing fibers, can provide a conditioner system that comprises an admixture of different polyethylene glycols in varying amounts. For example, from about 0.5% by weight of the restorative cleansing or conditioning system can comprise PEG 4000 and 0.5% by weight of the restorative cleansing or conditioning system can comprise PEG 8000.

One non-limiting example of a suitable conditioning agent includes polyethylene glycols having an average molecular weight from about 1200 g/mol to about 20,000 g/mol. A further example of a suitable conditioning agent includes the polyethylene glycols having an average molecular weight from about 3,000 g/mol to about 12,000 g/mol. Another example of a suitable conditioning agent includes the polyethylene glycols having an average molecular weight from about 4,000 g/mol to about 10,000 g/mol. One non-limiting example of a suitable conditioning agent is a polyethylene glycol having an average molecular weight of about 8,000 g/mol, for example, PEG 8000.

Another embodiment of conditioning agents relates to polypropylene glycols having the formula:

HO[CH(CH$_3$)CH$_2$O]$_x$H wherein the index x represent the average number of propyleneoxy units in the glycol polymer. As in the case of ethylene glycols, for propylene glycols the index x can be represented by a whole number or a fraction. For example, a polypropylene glycol having an average molecular weight of 8,000 g/mole (PEG 8000) can be equally represented by the formulae:

HO[CH(CH$_3$)CH$_2$O]$_{138}$H or HO[CH(CH$_3$)CH$_2$O]$_{137.6}$H or the polypropylene glycol can be represented by the common, short hand notation: PPG 8000.

One non-limiting example of the disclosed conditioning agents includes polypropylene glycols having an average molecular weight from about 1200 g/mol to about 20,000 g/mol. A further example of the disclosed conditioning agents includes the polypropylene glycols having an average molecular weight from about 3,000 g/mol to about 12,000 g/mol. Another example of the disclosed conditioning agents includes the polypropylene glycols having an average molecular weight from about 4,000 g/mol to about 10,000 g/mol. One non-limiting example of the disclosed conditioning agents includes a polypropylene glycol having an average molecular weight of about 8,000 g/mol, for example, PER 8000.

Polypropylene glycols can be admixed with polyethylene glycols to form a conditioning agent system for use in the disclosed restorative cleansing or conditioning systems.

A further example of conditioning agents includes poloxamers having the formula:

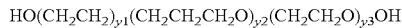

$HO(CH_2CH_2)_{y1}(CH_2CH_2CH_2O)_{y2}(CH_2CH_2O)_{y3}OH$ these are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol. These nonionic conditioning agents are also well known by the trade name PLURONICS™ These compounds are commonly named with the word Poloxamer followed by a number to indicate the specific co-polymer, for example Poloxamer 407 having two PEG blocks of about 101 units ($y^1$ and $y^3$ each equal to 101) and a polypropylene block of about 56 units. This extracellular desiccant is available from BASF under the trade name LUTROL™ F-17.

One iteration of this embodiment relates to restorative cleansing or conditioning systems that comprise form about 0.1% to about 1.0% by weight of poloxamer 185 [CAS Reg. No. 9003-11-6] wherein the indices $y^1$, $y^2$, and $y^3$ have the average values of 19, 30 and 10 respectively.

In another aspect, the disclosed compositions can comprise a restorative cleansing or conditioning system comprising lysine as a conditioning agent. The disclosed compositions can comprise from about 0.0001% to about 1% by weight of lysine. In one aspect, the compositions comprise from about 0.005% to about 0.5% by weight of lysine.
 i) from about 0.005% to about 0.5% by weight of lysine; and
 ii) from about 0.1% to about 1.0% by weight of poloxamer 185.

Adjunct Ingredients

In addition to the disclosed color precursors, detangling agents, UV radiation absorbers, and lysine, the disclosed compositions can further comprise one or more adjunct ingredients. Non-limiting examples of adjunct ingredients include moisturizers, chelating agents, anti-oxidation agents, pH adjusters, emulsifiers, shine agents, solubilizers, fragrances, pearlizers, and the like.

In a further embodiment, the restorative cleansing or conditioning systems that comprise the disclosed compositions can comprise the following adjunct ingredients:
 i) pearlizers, for example, Mica (and) CI 77891 (and) Triethoxycaprylylsilane sold as Covapearl™ Silver 939AS available from Sensient/LCW;
 ii) amino acid comprising adjunct ingredients comprising admixtures of amino acids, for example, Prodew™ available from Ajinomoto,
 iii) keratin-containing fiber benefit ingredients, for example, Helianthus Annuus (Sunflower) Seed Oil and Caviar Extract sold as Lipidami™ Caviar available from Alban Muller,
 iv) one or more opacifiers, for example glycol distearate sold as Mackester™ EGDS available from McIntyre Chemicals.

The following are non-limiting examples of UV protectants suitable for use in the disclosed compositions: Aminobenzoic Acid, Cinoxate, Diethanolamine Methoxy-cinnamate, Digalloyl Trioleate, Dioxybenzone, Ethyl 4-[bis (Hydroxypropyl)]Aminobenzoate, Glyceryl Aminobenzoate, Homosalate, Lawsone with Dihydroxyacetone, Menthyl Anthranilate, Octocrylene, Octyl Methoxycinnamate, Octyl Salicylate, Oxybenzone, Padimate O, Phenylbenzimidazole Sulfonic Acid, Red Petrolatum, Sulisobenzone, Titanium Dioxide, and Trolamine Salicylate, cetaminosalol, Allatoin PABA, Benzalphthalide, Benzophenone, Benzophenone 1-12, 3-Benzylidene Camphor, Benzylidenecamphor Hydrolyzed Collagen Sulfonamide, Benzylidene Camphor Sulfonic Acid, Benzyl Salicylate, Bornelone, Bumetriozole, Butyl Methoxydibenzoyl-methane, Butyl PABA, Ceria/Silica, Ceria/Silica Talc, Cinoxate, DEA-Methoxycinnamate, Dibenzoxazol Naphthalene, Di-t-Butyl Hydroxybenzylidene Camphor, Digalloyl Trioleate, Diisopropyl Methyl Cinnamate, Dimethyl PABA Ethyl Cetearyldimonium Tosylate, Dioctyl Butamido Triazone, Diphenyl Carbomethoxy Acetoxy Naphthopyran, Disodium Bisethylphenyl Tiamminotriazine Stilbenedisulfonate, Disodium Distyrylbiphenyl Triaminotriazine Stilbenedisulfonate, Disodium Distyrylbiphenyl Disulfonate, Drometrizole, Drometrizole Trisiloxane, Ethyl Dihydroxypropyl PABA, Ethyl Diisopropylcinnamate, Ethyl Methoxycinnamate, Ethyl PABA, Ethyl Urocanate, Etrocrylene Ferulic Acid, Glyceryl Octanoate Dimethoxycinnamate, Glyceryl PABA, Glycol Salicylate, Homosalate, Isoamyl p-Methoxycinnamate, Isopropylbenzyl Salicylate, Isopropyl Dibenzolylmethane, Isopropyl Methoxycinnamate, Menthyl Anthranilate, Menthyl Salicylate, 4-Methylbenzylidene, Camphor, Octocrylene, Octrizole, Octyl Dimethyl PABA, Octyl Methoxycinnamate, Octyl Salicylate, Octyl Triazone, PABA, PEG-25 PABA, Pentyl Dimethyl PABA, Phenylbenzimidazole Sulfonic Acid, Polyacrylamidomethyl Benzylidene Camphor, Potassium Methoxycinnamate, Potassium Phenylbenzimidazole Sulfonate, Red Petrolatum, Sodium Phenylbenzimidazole Sulfonate, Sodium Urocanate, TEA-Phenylbenzimidazole Sulfonate, TEA-Salicylate, Terephthalylidene Dicamphor Sulfonic Acid, Titanium Dioxide, Zinc Dioxide, Serium Dioxide, TriPABA Panthenol, Urocanic Acid, and VA/Crotonates/Methacryloxy-benzophenone-1 Copolymer.

CLEANSING COMPOSITIONS

Disclosed herein are color protectant cleansing compositions that maintain the color fastness of dyed, colored, or tinted keratin-containing fibers while providing fiber integrity and health. In general, the color protectant conditioner composition comprises, in order of addition:
 A) from about 40% to about 60% by weight of a stabilized carrier system, comprising:
  a) from about 0.01% to about 5% by weight of one or more aqueous solution stabilizers or thickeners; and
  b) the balance one or more carriers;
 B) from about 30% to about 60% by weight of a surface active component, comprising:
  a) from about 65% to about 99% by weight of surfactant, containing:
   i) from about 25% to about 60% by weight of one or more anionic surfactants;
   ii) from about 15% to about 35% by weight of one or more zwitterionic (amphoteric) surfactants;
   iii) from about 1% to about 10% by weight of one or more nonionic surfactants; and
   iv) from about 5% to about 15% by weight of one or more cationic surfactants;
  b) from about 0.1% to about 3% by weight of one or more preservatives, bactericidal, bacteriostatic compounds, and mixtures thereof;
  c) from about 1% to about 10% by weight of one or more wetting agents, rinse aids, chelants, emollients, foaming agents, and humectants; and C) from about 1% to about 5% by weight of keratin-containing fiber compatible adjunct ingredients.

The disclosed restorative hair cleansing, conditioning, and maintenance compositions contain a surfactant system, said surfactant system comprising:
a) from about 25% to about 75% by weight of one or more anionic surfactants;
b) from about 15% to about 35% by weight of one or more zwitterionic (amphoteric) surfactants;
c) from about 1% to about 10% by weight of one or more nonionic surfactants; and
d) from about 5% to about 15% by weight of one or more cationic surfactants.

In one aspect, the surfactant system comprises:
a) from about 55% to about 75% by weight of one or more anionic surfactants chosen from:
  i) $C_{10}$-$C_{18}$ alkyl alkoxy sulfates having the formula:

$$CH_3(CH_2)_x(OCH_2CH_2)_yOSO_3M$$

wherein the index x is from 9 to 17, y is from 1 to 7 and M is a water soluble cation chosen from ammonium, lithium, sodium, potassium and mixtures thereof; and
  ii) $C_{10}$-$C_{18}$ alkenyl sulfonates (α-olefin sulfonates) having the formula:

$$CH_3(CH_2)_zCH{=}CHSO_3M$$

wherein the index z is from 7 to 15 and M is a water soluble cation chosen from ammonium, lithium, sodium, potassium and mixtures thereof;
b) from about 15% to about 35% by weight of one or more $C_{10}$-$C_{16}$ alkyl amide betaine zwitterionic surfactants having the formula:

$$CH_3(CH_2)_wC(O)NH(CH_2)_uN^+(CH_3)_2(CH_2)_tCO_2^-$$

wherein the index w is from 9 to 15, the index u is from 1 to 5 and the index t is from 1 to 5; and
c) from about 0.5% to about 10% by weight of a $C_8$-$C_{18}$ alkylglycosidyl nonionic surfactant having the formula:

$$CH_3(CH_2)_qO[G]_pH$$

wherein G represents a monosaccharide residue chosen from glucose, fructose, mannose, galactose, talose, allose, altrose, idose, arabinose, xylose, lyxose, ribose and mixtures thereof, the index q is from 7 to 17.

One embodiment of this aspect of the surfactant system relates to surfactant systems comprising:
a) from about 45% to about 55% by weight of one or more anionic surfactants chosen from:
  i) sodium $C_{1-2}$ alkyl alkoxy sulfate; and
  ii) sodium $C_{14}$-$C_{16}$ alkenyl sulfonate;
b) from about 20% to about 30% by weight of one or more $C_{10}$-$C_{16}$ alkyl amide betaine zwitterionic surfactants chosen from {[3-(decanoylamino)ethyl]-(dimethyl)ammonio}acetate, {[3-(decanoylamino)ethyl](dimethyl)ammonio}-acetate, {[3-(dodecanoylamino)ethyl](dimethyl)ammonio}acetate, {[3-(dodecanoylamino)propyl](dimethyl)ammonio}acetate, {[3-(dodecanoylamino)-butyl](dimethyl)ammonio}acetate, {[3-(tetradecanoylamino)ethyl](dimethyl)ammonio}acetate, {[3-(tertadecanoylamino)propyl](dimethyl)ammonio}acetate, {[3-(hexadecanoylamino)ethyl](dimethyl)ammonio}acetate, and {[3-(hexadecanoylamino)propyl](dimethyl)ammonio}acetate; and c) from about 1.5% to about 5.5% by weight of a $C_8$-$C_{18}$ alkylglycosidyl nonionic chosen from n-octyl β-D-glucopyranoside, n-decyl β-D-glucopyranoside, n-dodecyl β-D-glucopyranoside, n-tetradecyl β-D-glucopyranoside, n-octyl β-D-maltopyranoside, n-decyl β-D-maltopyranoside, n-dodecyl β-D-maltopyranoside, n-tetradecyl β-D-maltopyranoside, n-octyl β-D-mannopyranoside, n-decyl β-D-mannopyranoside, n-dodecyl β-D-mannopyranoside and n-tetradecyl β-D-mannopyranoside.

Another iteration of this embodiment comprises:
a) from about 55% to about 70% by weight of one or more anionic surfactants chosen from:
  i) one or more $C_{14}$-$C_{16}$ alkyl alkoxy sulfates; and
  ii) one or more $C_{10}$-$C_{12}$ alkenyl sulfonates;
b) from about 25% to about 40% by weight of one or more $C_{12}$-$C_{14}$ alkyl amide betaine zwitterionic surfactants; and
c) from about 0.5% to about 3% by weight of a $C_{12}$-$C_{14}$ alkylglucoside nonionic surfactant.

Phase A

Phase A of the disclosed cleansing compositions comprises a stabilized carrier system. In one embodiment, Phase A comprises water comprising from about 0.01% to about 2% by weight of one or more stabilizers or thickeners. The following are non-limiting examples of Phase A suitable for use in the disclosed cleansing compositions.

TABLE I

| Ingredients | A1 | A2 | A3 | A4 | A5 |
|---|---|---|---|---|---|
| Guar gum, 2-hydroxy-3-(trimethylammonio)propylether chloride | 0.31 | 0.38 | 0.4 | 0.35 | 0.6 |
| water | balance | balance | balance | balance | balance |

Phase B

Phase B comprises a surfactant system and other surface active agents, inter alia, foaming agents, emollients, rinse aids, wetting agents, as well as preservatives and preservative combinations. One preservative combination that can be used in the disclosed compositions relates to a bactericide, for example, phenoxyethanol in combination with a quaternary ammonium compound, for example, an antistatic agent such as PG-hydroxyethyl cellulose cocodiammonium chloride (introduced in Phase C) or a highly charged cationic compound such as polyquartenium-87. The following are non-limiting examples of Phase B suitable for use in the disclosed cleansing compositions.

TABLE II

| Ingredients | B1 | B2 | B3 | B4 | B5 |
|---|---|---|---|---|---|
| glycerin | 2 | 2 | 2 | 2 | 2.1 |
| {[3-(dodecanoylamino)propyl]-(dimethyl)ammonio}acetate | 25 | 25 | 30 | 21 | 28 |
| cocamide DEA | 6 | 6 | 6 | 8.4 | 6.5 |
| alkyl glucoside | 2.9 | 4 | 4 | 10 | 3.3 |
| imidazolidinyl urea | 1 | 1 | 1 | 1 | 1 |
| sodium $C_{14}$-$C_{16}$ olefin sulfonate | 2 | 4 | 4 | 3 | 2.2 |
| glycol distearate | 5 | 5 | 5 | 6 | 5.4 |
| polyquaternium-87 | 1 | 1 | 1 | 1 | 1 |
| EDTA | 1 | 1 | 1 | 1 | 1 |
| PEG-12 dimethicone | 2 | 2 | 2 | 2 | 2 |
| 1,3-bis(hydroxymethyl)-5,5-dimethylimidazolidine-2,4-dione | 1 | 1 | 1 | 1 | 1 |

TABLE II-continued

| Ingredients | B1 | B2 | B3 | B4 | B5 |
|---|---|---|---|---|---|
| sodium laureth sulfate | 49 | 45 | 40 | 40 | 54.2 |
| phenoxyethanol | 1 | 1 | 1 | 1 | 1 |
| PPG-5 Ceteth-29 | 1 | 1 | 1 | 1 | 1 |

Phase C

Phase C comprises fiber compatible adjunct ingredients, for example, amino acids, skin integrity agents, moisturizers, antioxidants, fragrances, dyes, and the like.

TABLE III

| Ingredients | C1 | C2 | C3 | C4 | C5 |
|---|---|---|---|---|---|
| Fragrance oils | 28.5 | 29.4 | 32.3 | 29.8 | 34.7 |
| PEG-8 dimethicone | 15.7 | 17.64 | 14.5 | 14.9 | 19.1 |
| PG-hydroxyethyl cellulose cocodiammonium chloride | 14.2 | 11.8 | 16.1 | 14.9 | 17.4 |
| Potassium cocoyl glycinate | 17.1 | 17.6 | 19.4 | 14.9 | 20.8 |
| Oat amino acids | 14.2 | 14.7 | 16.1 | 14.9 | 17.4 |
| helianths annuus seed oil and caviar exract | 14.2 | 1.5 | 1.6 | 1.5 | 1.7 |
| Photoprotectant | 0.3 | 0.03 | 0.03 | 0.3 | 0.03 |
| Colorant | 8.5 | 8.8 | 9.7 | 8.9 | 10.4 |

EXAMPLES

The following are non-limiting examples of compositions useful for treating damaged keratin-containing fibers. Examples 1-5 were prepared by the general procedure as follows. The disclosed examples can be used on any type of keratin-containing fiber, especially human hair, either by a single user or applied by a professional, i.e., a stylist. The restorative effects produced on keratin-containing fibers are reproducible, as well as cumulative when applied as necessary or directed.

Phase A was prepared by charging a reaction vessel with water (9969 g) and slowly adding and dissolving Guar gum, 2-hydroxy-3-(trimethylammonio)propylether chloride (31 g) to form Phase A1 as disclosed in Table I. Once dissolved, the solution was heated to from 70° C. to about 80° C. and the components of Phase B as exemplified in Example B2 are added in the following order and amounts as listed in Table IV. The amounts given in Table IV are the amounts of the listed trade name products and, as such, each ingredient can include water.

For example polyquaternium-87 comprises 26% solids by weight of polyquaternium-87 and the balance water as a carrier.

TABLE IV

| Ingredients | Trade name | Amount (g) |
|---|---|---|
| glycerin | — | 206.2 |
| {[3-(dodecanoylamino)propyl]-(dimethyl)ammonio}acetate | Jeeteric ™ CAB-LC | 2474.2 |
| cocamide DEA | Mackamide ™ DEA | 618.6 |
| alkyl glucoside | Plantacare ™ 818 | 412.4 |
| imidazolidinyl urea | Germall ™ 115 | 103.1 |
| sodium $C_{14}$-$C_{16}$ olefin sulfonate | Bio-Terge ™ AS-40 | 412.4 |
| glycol distearate | Macester ™ EGDS | 515.5 |
| polyquaternium-87 | Luviquat ™ Sensation | 103.1 |
| EDTA | Dissolvin ™ ZS | 103.1 |
| PEG-12 dimethicone | DC Surfactant ™ 193C | 206.2 |
| 1,3-bis(hydroxymethyl)-5,5-dimethylimidazolidine-2,4-dione | Mackstart ™ DM | 102.1 |
| sodium laureth sulfate | Texapon ™ N-56 | 4536.1 |
| phenoxyethanol | Seppicide ™ | 103.1 |
| PPG-5 Ceteth-29 | Procetyl ™ AWS | 103.1 |

Following the addition of PPG-5 Ceteth-29, mixing was continued for an additional 30 minutes after which the solution was cooled to 45° C. to 50° C. Once cooled the components of Phase C as exemplified in Example C1 are added in the following order and amounts shown in Table V.

TABLE V

| Ingredients | Trade name | Amount (g) |
|---|---|---|
| Fragrance oil | — | 206.8 |
| Peg-8 dimethicone | Biowax ™ Liquid 754 | 103.4 |
| PG-hydroxyethyl cellulose cocodiammonium chloride | Crodacel ™ QM | 103.4 |
| potassium cocoyl glycinate | Amilite ™ GCK-12 | 103.4 |
| oat amino acid | Amino Oat ™ | 103.4 |
| helianths annuus seed oil and caviar exract | Lipidami ™ Caviar | 10.3 |
| UV protectant | Covabsorb ™ EW | 2 |
| colorant | — | 62.1 |
| Total | | 694.8 |

After the addition of the colorant was complete the admixture was stirred while cooling to about 30° C. until the color effect was homogeneous. The resulting composition was a gel having a white pearlized cream color, a specific gravity of 1.06 g/mL, pH of 7.71, and a viscosity of 6,220 cps. In a like manner, Phase A2 (45 equiv.), Phase B1 (51 equiv.) and Phase C1 (3.51 equiv.) are combined to produce the composition of Example 2. In a similar like manner, Phase A3 (45 equiv.), Phase B3 (51 equiv.) and Phase C2 (3.51 equiv.) are combined to produce the composition of Example 3. Similarly, Phase A4 (45 equiv.), Phase B4 (51 equiv.) and Phase C4 (3.51 equiv.) are combined to produce the composition of Example 4. As describe above, Phase A5 (45 equiv.), Phase B5 (51 equiv.) and Phase C5 (3.51 equiv.) are combined to produce the composition of Example 5. The resulting compositions Examples 1-5 comprise the following ingredients in the following approximate amounts on a % weight/weight basis.

TABLE VI

| Ingredients | 1 | 2 | 3 | 4 | 5 |
|---|---|---|---|---|---|
| guar hydroxypropyl triammonium chloride | 0.15 | 0.17 | 0.2 | 0.17 | 0.3 |
| glycerin | 1 | 1 | 1 | 1 | 1 |
| {[3-(dodecanoylamino)propyl]-(dimethyl)ammonio}acetate | 12 | 13 | 15 | 10.5 | 13 |
| cocamide DEA | 3 | 3 | 3 | 4.2 | 3 |
| alkyl glucoside | 2 | 1.5 | 2 | 5 | 1.5 |
| imidazolidinyl urea | 0.5 | 0.5 | 0.5 | 0.5 | 0.5 |
| sodium $C_{14}$-$C_{16}$ olefin sulfonate | 2 | 1 | 2 | 1.5 | 1 |
| glycol distearate | 2.5 | 2.5 | 2.5 | 3 | 2.5 |
| polyquaternium-87 | 0.5 | 0.5 | 0.5 | 0.5 | 0.5 |
| EDTA | 0.5 | 0.5 | 0.5 | 0.5 | 0.5 |
| PEG-12 dimethicone | 1 | 1 | 1 | 1 | 1 |
| 1,3-bis(hydroxymethyl)-5,5-dimethylimidazolidine-2,4-dione | 0.5 | 0.5 | 0.5 | 0.5 | 0.5 |
| sodium laureth sulfate | 22 | 25 | 20 | 20 | 25 |
| phenoxyethanol | 0.5 | 0.5 | 0.5 | 0.5 | 0.5 |
| PPG-5 Ceteth-29 | 0.5 | 0.5 | 0.5 | 0.5 | 0.5 |
| Fragrance oil | 1 | 1 | 1 | 1 | 1 |
| Peg-8 dimethicone | 0.5 | 0.55 | 0.6 | 0.45 | 0.55 |

TABLE VI-continued

| Ingredients | 1 | 2 | 3 | 4 | 5 |
|---|---|---|---|---|---|
| PG-hydroxyethyl cellulose cocodiammonium chloride | 0.5 | 0.5 | 0.34 | 0.5 | 0.5 |
| potassium cocoyl glycinate | 0.5 | 0.6 | 0.6 | 0.6 | 0.6 |
| oat amino acid | 0.5 | 0.5 | 0.5 | 0.5 | 0.5 |
| helianths annuus seed oil and caviar exract | 0.05 | 0.05 | 0.05 | 0.05 | 0.05 |
| colorant | 0.3 | 0.3 | 0.3 | 0.3 | 0.3 |
| Coabsorb ™ EW | 0.01 | 0.01 | 0.01 | 0.01 | 0.01 |
| water | balance | balance | balance | balance | balance |

CONDITIONING COMPOSITIONS

Disclosed herein are color protectant conditioners that maintain the color fastness of dyed, colored, or tinted keratin-containing fibers while providing fiber integrity and health. In general, the color protectant conditioner composition comprises, in order of addition:

A) from about 60% to about 99% by weight of a stabilized carrier system, comprising:
  a) from about 0.01% to about 5% by weight of one or more aqueous solution stabilizers or thickeners; and
  b) the balance one or more carriers;
B) from about 2% to about 50% by weight of a surface active component, comprising:
  a) from about 10% to about 80% by weight of an emulsion system, containing:
    i) from about 1% to about 35% by weight of one or more emulsifiers;
    ii) from about 1% to about 35% by weight of one or more emulsion stabilizers;
    iii) from about 5% to about 90% by weight of one or more surfactants; and
    iv) the balance one or more compatible carriers;
  b) from about 1% to about 50% by weight of one or more emollients, humectants, lubricants, and mixtures thereof; and
  c) from about 1% to about 10% by weight of one or more anti-bacterial, bactericidal, bacteriostatic compounds, and mixtures thereof; and
C) from about 0.01% to about 5% by weight of keratin-containing fiber compatible adjunct ingredients.

Phase A

Phase A comprises a stabilized carrier system. In one embodiment, Phase A comprises water comprising from about 0.01% to about 5% by weight of one or more stabilizers or thickeners. The following are non-limiting examples of Phase A suitable for use in the disclosed colorant protectant compositions.

TABLE VII

| Ingredients | A6 | A7 | A8 | A9 | A10 |
|---|---|---|---|---|---|
| Guar gum, 2-hydroxy-3-(trimethylammonio)propylether chloride | 0.38 | 0.3 | 0.45 | 0.4 | 0.72 |
| water | balance | balance | balance | balance | balance |

TABLE VIII

| Ingredients | A11 | A12 | A13 | A14 | A15 |
|---|---|---|---|---|---|
| Guar gum, 2-hydroxy-3-(trimethylammonio)propylether chloride | 0.38 | 0.3 | 0.45 | 0.4 | 0.72 |
| water | balance | balance | balance | balance | balance |

Phase B

Phase B comprises an emulsion system that contains one or more emulsifiers, emulsion stabilizers, surfactants, emollients, humectants and the like that can form a protective layer on keratin-containing fibers while effectively delivering one or more compounds that assist in restoring the fibers to its pre-damaged state. The following are non-limiting examples of Phase B suitable for use in the disclosed colorant protectant compositions.

TABLE IX

| Ingredients | B6 | B7 | B8 | B9 | B10 |
|---|---|---|---|---|---|
| Triethanolamine | 1 | 1.5 | 2 | 1 | 1.5 |
| 2-hydroxy-N-(2-hydroxyethyl)-propanamide | 2.5 | 1.5 | 1.5 | 2.5 | 2 |
| PEG-12 dimethicone | 2.5 | 3 | 2.5 | 2.5 | 2.5 |
| Cetearyl alcohol dicetyl phosphate ceteth-10 phosphate | 20 | 27 | 25 | 20 | 22.5 |
| Cetearyl alcohol | 20 | 18 | 15 | 18 | 17.5 |
| Imidazolidinyl urea | 2.5 | 2.5 | 2.5 | 2.5 | 2 |
| Phenoxyethanol | 2.5 | 2.5 | 2.5 | 2.5 | 3 |
| Stearalkonum chloride | 35 | 25 | 30 | 37 | 35 |
| Glycol distearate | 10 | 15 | 15 | 10 | 10 |
| Cetyl trimethyl ammonium chloride | 2.5 | 2.5 | 2.5 | 2.5 | 2.5 |
| 1,3-Bis(hydroxymethyl)-5,5-dimethylimidazolidine-2,4-dione | 1.5 | 1.5 | 1.5 | 1.5 | 1.5 |

Phase C

Phase C comprises fiber compatible adjunct ingredients, for example, amino acids, skin integrity agents, moisturizers, antioxidants, fragrances, dyes, and the like. The following are non-limiting examples of Phase C suitable for use in the disclosed colorant protectant compositions.

TABLE X

| Ingredients | C6 | C7 | C8 | C9 | C10 |
|---|---|---|---|---|---|
| Safflower oleosomes | 25 | 22 | 20 | 20 | 25 |
| Fragrance | 50 | 50 | 50 | 50 | 50 |
| Amino Acids (PRODEW 500 ™) | 0.1 | 0.1 | 0.1 | 0.15 | 0.1 |
| Lipidami caviar | 2 | 3 | 5 | 5 | 5 |
| Cystine bis-PG-propylsilanetriol | 8 | 9.5 | 10 | 9 | 10 |
| Photoprotectant | 5 | 5.5 | 5 | 6 | 5 |
| Colorant | balance | balance | balance | balance | balance |

EXAMPLES

The following are non-limiting examples of compositions useful for treating damaged keratin-containing fibers. Examples 6-10 were prepared by the general procedure as follows. The disclosed examples can be used on any type of keratin-containing fiber, especially human hair, either by a single user or applied by a professional, i.e., a stylist. The restorative effects produced on keratin-containing fibers are reproducible, as well as cumulative when applied as necessary or directed.

Phase A was prepared by charging a reaction vessel with water (9962 g) and slowly adding and dissolving Guar gum, 2-hydroxy-3-(trimethylammonio)propylether chloride (38 g) to form Phase A6 as disclosed in Table VII. Once dissolved, the solution was heated to from 70° C. to about 80° C. and the components of Phase B as exemplified in Example B6 are added in the following order and amounts in Table XI

TABLE XI

| | |
|---|---|
| Triethanolamine | 25 g |
| 2-hydroxy-N-(2-hydroxyethyl)-propanamide | 62.5 g |
| PEG-12 dimethicone | 62.5 g |
| Cetearyl alcohol dicetyl phosphate ceteth-10 phosphate | 500 g |
| Cetearyl alcohol | 500 g |
| Imidazolidinyl urea | 62.5 g |
| Phenoxyethanol | 62.5 g |
| Stearalkonum chloride | 875 g |
| Glycol distearate | 250 g |
| Cetyl trimethyl ammonium chloride | 62.5 g |
| 1,3-Bis(hydroxymethyl)-5,5-dimethylimidazolidine-2,4-dione | 37.5 g |
| Total | 2500 g |

After the addition of 1,3-bis(hydroxymethyl)-5,5-dimethylimidazolidine-2,4-dione was complete, mixing was continued for an additional 30 minutes after which the solution was cooled to 45° C. to 50° C. Once cooled the components of Phase C as exemplified in Example C8 are added in the following order and amounts in Table XII

TABLE XII

| | |
|---|---|
| Safflower oleosomes | 25 g |
| Fragrance | 62.5 g |
| Amino Acids (PRODEW 500 ™) | 0.125 g |
| Lipidami caviar ™ | 6.25 g |
| Cystine bis-PG-propylsilanetriol | 12.5 g |
| Nano-Lipobelle UV-A/B ™ | 6.25 g |
| Covapearl Silver 939AS ™ | 12.375 g |
| Total | 125 g |

After the addition of the colorant was complete the admixture was stirred while cooling to about 30° C. until the color effect was homogeneous. The resulting composition had a white to off-white pearlized cream color, a specific gravity of 0.949 g/mL and pH of 3.32.

In a like manner, Phase A7, Phase B10 and Phase C7 are combined to produce the composition of Example 7. In a similar like manner, Phase A8, Phase B8 and Phase C8 are combined to produce the composition of Example 8. Similarly, Phase A6, Phase B10 and Phase C7 are combined to produce the composition of Example 9. As describe above, Phase A9, Phase B6 and Phase C8 are combined to produce the composition of Example 10. The resulting compositions Examples 1-5 comprise the following ingredients in the following approximate amounts on a % weight/weight basis.

TABLE XIII

| Ingredients | 6 | 7 | 8 | 9 | 10 |
|---|---|---|---|---|---|
| Guar hydroxypropyl ammonium chloride | 0.3 | 0.24 | 0.36 | 0.3 | 0.32 |
| Triethanolamine | 0.2 | 0.3 | 0.4 | 0.3 | 0.2 |
| 2-hydroxy-N-(2-hydroxyethyl)-propanamide | 0.5 | 0.4 | 0.3 | 0.4 | 0.5 |
| PEG-12 dimethicone | 0.5 | 0.5 | 0.5 | 0.5 | 0.5 |
| Cetearyl alcohol dicetyl phosphate ceteth-10 phosphate | 4 | 4.5 | 5 | 4.5 | 4 |
| Cetearyl alcohol | 4 | 3.5 | 3 | 3.5 | 4 |
| Imidazolidinyl urea | 0.5 | 0.4 | 0.5 | 0.4 | 0.5 |
| Phenoxyethanol | 0.5 | 0.6 | 0.5 | 0.6 | 0.5 |
| Stearalkonum chloride | 7 | 7 | 6 | 7 | 7 |
| Glycol distearate | 2 | 2 | 3 | 2 | 2 |
| Cetyl trimethyl ammonium chloride | 0.5 | 0.5 | 0.5 | 0.5 | 0.5 |
| 1,3-Bis(hydroxymethyl)-5,5-dimethyl-imidazolidine-2,4-dione | 0.5 | 0.3 | 0.3 | 0.3 | 0.5 |
| Safflower oleosomes | 0.2 | 0.22 | 0.2 | 0.22 | 0.2 |
| Colorant | 0.1 | 0.1 | 0.1 | 0.1 | 0.1 |
| Fragrance | 0.5 | 0.5 | 0.5 | 0.5 | 0.5 |
| Amino Acids (PRODEW 500 ™) | 0.001 | 0.001 | 0.001 | 0.001 | 0.001 |
| Lipidami caviar | 0.05 | 0.03 | 0.03 | 0.03 | 0.05 |
| Cystine bis-PG-propylsilanetriol | 0.1 | 0.1 | 0.1 | 0.1 | 0.1 |
| Photoprotectant | 0.05 | 0.5 | 0.5 | 0.5 | 0.05 |
| Water | balance | balance | balance | balance | balance |

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A keratin-containing fiber cleansing composition comprising:
   A) from about 25% to about 60% by weight of a surfactant system wherein the surfactant system comprises;
      a) from about 55% to about 75% by weight of one or more anionic surfactants chosen from:
         i) $C_{10}$-$C_{18}$ alkyl alkoxy sulfates having the formula:

$$CH_3(CH_2)_x(OCH_2CH_2)_yOSO_3M$$

wherein the index x is from 9 to 17, y is from 1 to 7 and M is a water soluble cation chosen from ammonium, lithium, sodium, potassium and mixtures thereof; and
         ii) $C_{10}$-$C_{18}$ alkenyl sulfonates (α-olefin sulfonates) having the formula:

$$CH_3(CH_2)_zCH=CHSO_3M$$

wherein the index z is from 7 to 15 and M is a water soluble cation chosen from ammonium, lithium, sodium, potassium and mixtures thereof;
      b) from about 15% to about 35% by weight of one or more $C_{10}$-$C_{16}$ alkyl amide betaine zwitterionic surfactants having the formula:

$$CH_3(CH_2)_wC(O)NH(CH_2)_uN^+(CH_3)_2(CH_2)_tCO_2^-$$

wherein the index w is from 9 to 15, the index u is from 1 to 5 and the index t is from 1 to 5; and
      c) from about 0.5% to about 10% by weight of a $C_8$-$C_{18}$ alkylglycosidyl nonionic surfactant having the formula:

$$CH_3(CH_2)_qO[G]_pH$$

wherein G represents a monosaccharide residue chosen from glucose, fructose, mannose, galactose, talose, allose, altrose, idose, arabinose, xylose, lyxose, ribose and mixtures thereof, the index q is from 7 to 17;

B) from about 0.5% to about 15% by weight of a composition modifier system comprising:
  a) from about 10% to about 50% by weight of one or more cationic polymeric thickeners;
  b) from about 25% to about 90% by weight of a foaming agent chosen from N-(2-hydroxyethyl)decanamide ($C_{10}$ alkyl monoethanolamine), N-(2-hydroxyethyl)-dodecanamide ($C_{12}$ alkyl monoethanolamine), cocamide MEA), and N-(2-hydroxyethyl)tetra-decanamide ($C_{16}$ alkyl monoethanolamine); and
  c) from about 5% to about 15% by weight of an aesthetic and preservative system comprising:
    i) from about 20% to about 70% by weight of one or more preservatives;
    ii) from about 0.01% to about 5% by weight of one or more UV protectants;
    iii) from about 10% to about 50% by weight of one or more pearlizing agents; and
    iv) from about 10% to about 50% by weight of one or more fragrances and colorants;

C) from about 0.5% to about 10% by weight of a keratin-containing fiber enhancement system comprising:
  a) from about 10% to about 50% by weight of 2-hydroxyN-(2-hydroxyethyl)propanamide;
  b) from about 10% to about 50% by weight of one or more wetting agents chosen from:
    i) PEG-12 Dimethicone;
    ii) polyalkyl or polyaryl siloxanes having the following formula:

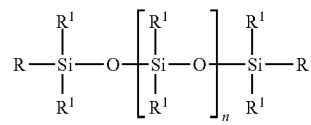

wherein R represents groups which block the ends of the silicone chains, $R^1$ is alkyl or aryl, and the index n is an integer from about 7 to about 8,000;
    iii) and mixtures thereof;
  c) from about 10% to about 50% by weight of an antistatic agent chosen from:
    i) laurdimonium hydroxyethylcellulose, cocodimonium hydroxyethylcellulose, steardimonium hydroxyethylcellulose and mixtures thereof; and
    ii) one or more polyquaternium agents chosen from polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-44, polyquaternium-27 and polyquaternium-55; and D) the balance one or more carriers.

\* \* \* \* \*